(12) United States Patent
Borkholder et al.

(10) Patent No.: US 10,292,445 B2
(45) Date of Patent: May 21, 2019

(54) EVENT MONITORING DOSIMETRY APPARATUSES AND METHODS THEREOF

(75) Inventors: David A. Borkholder, Canandaigua, NY (US); Werner Fassler, Rochester, NY (US); Andrew Blair, Corry, PA (US); Kim Sherman, Spencerport, NY (US); Derek DeBusschere, Los Gatos, CA (US)

(73) Assignee: ROCHESTER INSTITUTE OF TECHNOLOGY, Rochester, NY (US)

( * ) Notice: Subject to any disclaimer, the term of this patent is extended or adjusted under 35 U.S.C. 154(b) by 761 days.

(21) Appl. No.: 13/371,202

(22) Filed: Feb. 10, 2012

(65) Prior Publication Data

US 2012/0239343 A1   Sep. 20, 2012

Related U.S. Application Data

(60) Provisional application No. 61/446,369, filed on Feb. 24, 2011.

(51) Int. Cl.
*A42B 3/04* (2006.01)
*A61B 5/11* (2006.01)
(Continued)

(52) U.S. Cl.
CPC ............... *A42B 3/046* (2013.01); *A61B 5/11* (2013.01); *A61B 5/4064* (2013.01);
(Continued)

(58) Field of Classification Search
CPC . A42B 3/046; Y10T 29/046; Y10T 29/49002; A61B 5/11; A61B 5/4046;
(Continued)

(56) References Cited

U.S. PATENT DOCUMENTS

| 4,264,310 A | 4/1981 | Ashworth et al. |
| 5,117,695 A | 6/1992 | Henderson et al. |

(Continued)

FOREIGN PATENT DOCUMENTS

| EP | 1099389 A1 | 5/2001 |
| EP | 1408336 A3 | 6/2005 |

(Continued)

OTHER PUBLICATIONS

English translation for KR 100806876.*

(Continued)

*Primary Examiner* — Michael P Nghiem
*Assistant Examiner* — Dacthang P Ngo
(74) *Attorney, Agent, or Firm* — Bond, Schoeneck & King, PLLC; Joseph Noto

(57) ABSTRACT

A dosimetry apparatus includes at least one sensor in a housing, a cover configured to permit compression waves to pass through, the cover is seated over the at least one sensor, and a dosimetry processing device with a memory. The dosimetry processing device is coupled to the at least one sensor in the housing. The dosimetry processing device is configured to execute programmed instructions stored in the memory comprising: obtaining readings from the at least one sensor; storing the readings with a time and date stamp when obtained; conducting an analysis based on the obtained readings; and outputting at least one of the stored readings or the conducted analysis.

25 Claims, 6 Drawing Sheets

(51) Int. Cl.
*A61B 5/00* (2006.01)
*G01L 5/14* (2006.01)
*G01P 15/08* (2006.01)
*G16H 50/30* (2018.01)

(52) U.S. Cl.
CPC .......... *A61B 5/7275* (2013.01); *A61B 5/7282* (2013.01); *G01L 5/14* (2013.01); *G01P 15/0891* (2013.01); *G16H 50/30* (2018.01); *Y10T 29/49002* (2015.01)

(58) Field of Classification Search
CPC ....... A61B 5/7275; A61B 5/7282; G01L 5/14; G01P 15/0891; G16H 50/30
USPC ........................................................ 702/139
See application file for complete search history.

(56) References Cited

U.S. PATENT DOCUMENTS

| | | |
|---|---|---|
| 5,212,984 A | 5/1993 | Norling et al. |
| 5,220,838 A | 6/1993 | Fung et al. |
| 5,277,068 A | 1/1994 | Fukiura et al. |
| 5,357,808 A | 10/1994 | Fung et al. |
| 5,438,875 A | 8/1995 | Fung et al. |
| 5,524,489 A | 6/1996 | Twigg |
| 5,539,935 A | 7/1996 | Rush, III |
| 5,551,279 A | 9/1996 | Quick |
| 5,621,922 A | 4/1997 | Rush, III |
| 5,646,349 A | 7/1997 | Twigg et al. |
| 5,719,336 A | 2/1998 | Ando et al. |
| 5,723,787 A | 3/1998 | Stoddard et al. |
| 5,856,520 A | 1/1999 | Hirako et al. |
| 5,856,620 A | 1/1999 | Okada |
| 5,884,203 A | 3/1999 | Ross |
| 5,890,569 A | 4/1999 | Goepfert |
| 5,978,972 A | 11/1999 | Stewart et al. |
| 6,092,424 A | 7/2000 | Skinner et al. |
| 6,125,686 A | 10/2000 | Haan et al. |
| 6,178,820 B1 | 1/2001 | Kirjavainen et al. |
| 6,301,718 B1 | 10/2001 | Rigal |
| 6,307,481 B1 | 10/2001 | Lehrman et al. |
| 6,349,201 B1 | 2/2002 | Ford |
| 6,397,151 B1 | 5/2002 | Yamagishi et al. |
| 6,501,386 B2 | 12/2002 | Lehrman et al. |
| 6,584,852 B2 | 7/2003 | Suzuki et al. |
| 6,661,347 B2 | 12/2003 | Lehrman et al. |
| 6,703,939 B2 | 3/2004 | Lehrman et al. |
| 6,711,951 B2 | 3/2004 | Kicher et al. |
| 6,730,047 B2 | 5/2004 | Socci et al. |
| 6,798,392 B2 | 9/2004 | Hartwell et al. |
| 6,826,509 B2 | 11/2004 | Crisco, III et al. |
| 6,864,796 B2 | 3/2005 | Lehrman et al. |
| 6,941,952 B1 | 9/2005 | Rush, III |
| 7,054,784 B2 | 5/2006 | Flentov et al. |
| 7,095,331 B2 | 8/2006 | Lehrman et al. |
| 7,145,461 B2 | 12/2006 | Lehrman et al. |
| 7,150,048 B2 | 12/2006 | Buckman |
| 7,150,191 B2 | 12/2006 | Foote et al. |
| 7,162,392 B2 | 1/2007 | Vock et al. |
| 7,194,903 B2 | 3/2007 | Dwyer |
| 7,194,905 B2 | 3/2007 | Yamamoto et al. |
| 7,318,349 B2 | 1/2008 | Vaganov et al. |
| 7,378,954 B2 | 5/2008 | Wendt |
| 7,384,380 B2 | 6/2008 | Reinbold et al. |
| 7,386,401 B2 | 6/2008 | Vock et al. |
| 7,404,324 B2 | 7/2008 | Braman et al. |
| 7,478,108 B2 | 1/2009 | Townsend et al. |
| 7,479,890 B2 | 1/2009 | Lehrman et al. |
| 7,526,389 B2 | 4/2009 | Greenwald et al. |
| 7,540,193 B2 | 6/2009 | Sato et al. |
| 7,609,156 B2 | 10/2009 | Mullen |
| 7,660,692 B2 | 2/2010 | Van Albert et al. |
| 7,693,668 B2 | 4/2010 | Vock et al. |
| 7,747,415 B1 | 6/2010 | Churchill et al. |
| 7,836,771 B2 | 11/2010 | Killion |
| 7,845,226 B2 | 12/2010 | Ohkoshi |
| 7,849,740 B2 | 12/2010 | Nichol |
| 7,992,421 B2 | 8/2011 | Jeftic-Stojanovski et al. |
| 8,056,391 B2 | 11/2011 | Petelenz et al. |
| 8,079,247 B2 | 12/2011 | Russell et al. |
| 8,145,441 B2 * | 3/2012 | Xi .................. 702/41 |
| 2003/0197608 A1 | 10/2003 | Rudhard et al. |
| 2004/0200967 A1 | 10/2004 | Russell |
| 2005/0177335 A1 | 8/2005 | Crisco, III et al. |
| 2005/0177929 A1 | 8/2005 | Greenwald et al. |
| 2006/0038694 A1 | 2/2006 | Nauheim et al. |
| 2006/0074338 A1 | 4/2006 | Greenwald et al. |
| 2006/0189852 A1 | 8/2006 | Greenwald et al. |
| 2007/0056081 A1 | 3/2007 | Aspray |
| 2007/0079149 A1 | 4/2007 | Sahu et al. |
| 2007/0113702 A1 | 5/2007 | Braman et al. |
| 2007/0144396 A1 | 6/2007 | Hamel et al. |
| 2008/0006093 A1 | 1/2008 | Ueya |
| 2008/0072088 A1 | 3/2008 | Allarey et al. |
| 2008/0151456 A1 | 6/2008 | Julicher |
| 2008/0256687 A1 | 10/2008 | Spencer |
| 2008/0281234 A1 | 11/2008 | Goris et al. |
| 2009/0000377 A1 | 1/2009 | Shipps et al. |
| 2009/0090190 A1 | 4/2009 | Ueya |
| 2009/0185700 A1 | 7/2009 | Suzuki |
| 2009/0245565 A1 * | 10/2009 | Mittleman ............ H04M 1/035 381/365 |
| 2010/0005571 A1 | 1/2010 | Moss et al. |
| 2010/0016685 A1 | 1/2010 | Muehlsteff et al. |
| 2010/0072380 A1 | 3/2010 | Britton, Jr. et al. |
| 2010/0073678 A1 | 3/2010 | Smith et al. |
| 2010/0090643 A1 * | 4/2010 | Mardirossian ......... F03D 9/021 320/101 |
| 2010/0096556 A1 | 4/2010 | Arsalan et al. |
| 2010/0098269 A1 | 4/2010 | Abolfathi et al. |
| 2010/0098270 A1 | 4/2010 | Abolfathi et al. |
| 2010/0102970 A1 | 4/2010 | Hertz |
| 2010/0121226 A1 | 5/2010 | Ten Kate et al. |
| 2010/0171514 A1 | 7/2010 | Bernstein |
| 2010/0179389 A1 | 7/2010 | Moroney, III et al. |
| 2010/0227545 A1 * | 9/2010 | Frois ............................ 454/358 |
| 2010/0229784 A1 | 9/2010 | Bayne et al. |
| 2010/0257932 A1 | 10/2010 | Braman et al. |
| 2010/0275676 A1 | 11/2010 | King et al. |
| 2010/0307223 A1 * | 12/2010 | Jeftic-Stojanovski ...................... G01L 5/0052 73/12.04 |
| 2010/0326192 A1 | 12/2010 | Petelenz et al. |
| 2011/0012759 A1 | 1/2011 | Yin |
| 2011/0024640 A1 | 2/2011 | Kahilainen et al. |
| 2011/0077865 A1 | 3/2011 | Chen et al. |
| 2011/0098934 A1 | 4/2011 | Hubler et al. |
| 2011/0144539 A1 | 6/2011 | Ouchi |
| 2011/0144542 A1 | 6/2011 | Jin et al. |
| 2011/0152727 A1 | 6/2011 | Ten Kate |
| 2011/0162433 A1 | 7/2011 | Peng et al. |
| 2011/0162451 A1 * | 7/2011 | Petelenz et al. ........... 73/514.01 |
| 2011/0181418 A1 | 7/2011 | Mack et al. |
| 2011/0181419 A1 | 7/2011 | Mack et al. |
| 2011/0181420 A1 | 7/2011 | Mack et al. |
| 2011/0184319 A1 | 7/2011 | Mack et al. |
| 2011/0199216 A1 | 8/2011 | Flinsenberg et al. |
| 2011/0201972 A1 | 8/2011 | Ten Kate |
| 2011/0203347 A1 | 8/2011 | Hower et al. |
| 2011/0230791 A1 | 9/2011 | Ten Kate et al. |
| 2011/0231145 A1 | 9/2011 | Chen |
| 2011/0246114 A1 | 10/2011 | Jin |
| 2011/0283791 A1 | 11/2011 | Jeftic-Stojanovski et al. |
| 2011/0290018 A1 | 12/2011 | Jeftic-Stojanovski et al. |
| 2012/0109575 A1 | 5/2012 | Balbus et al. |
| 2012/0177237 A1 * | 7/2012 | Shukla ................ B29C 45/1671 381/332 |
| 2012/0272829 A1 * | 11/2012 | Fox et al. ...................... 96/154 |

(56) References Cited

U.S. PATENT DOCUMENTS

2013/0118255 A1* 5/2013 Callsen .................. A42B 3/046
                                                          73/491

FOREIGN PATENT DOCUMENTS

| EP | 2136215 | A2 | | 12/2009 |
|---|---|---|---|---|
| KR | 100806876 | | * | 2/2008 |
| WO | 2007083329 | A1 | | 7/2007 |
| WO | 2009026903 | A1 | | 3/2009 |
| WO | 2009070886 | A1 | | 6/2009 |
| WO | 2009121000 | | | 10/2009 |

OTHER PUBLICATIONS

PCT International Search Report; PCT/US2012/026622 dated Dec. 26, 2012.

PCT Written Opinion of the International Seraching Authority;PCT/US2012/026622 dated Dec. 26, 2012.

Riel et al., "Self-Indicating Radiation Alert Dosemeter (SIRAD)," Radiation Protection Dosimetry, 2006, pp. 1-4, doi: 10.1093/rpd/nci541, Oxford University Press.

Rochester Institute of Technology, "Faculty Connects Technology and Physiology to Improve Information about Effects of Explosive Blasts; Wearable Blast Dosimeter for Soldiers Measures Pressure and Head Acceleration," Athenaeum Article, 2 pages, October/November Issue.

International Search Written Opinion EPO Form 1703 01.91TRI, International Application No. 12 748 961.5, dated May 31, 2010, pp. 1-4.

Springer, Oliver, "Supplementary European Search Report" dated May 30, 2017, pp. 1-2, Application No. EP 12 74 896, Munich, Germany.

* cited by examiner

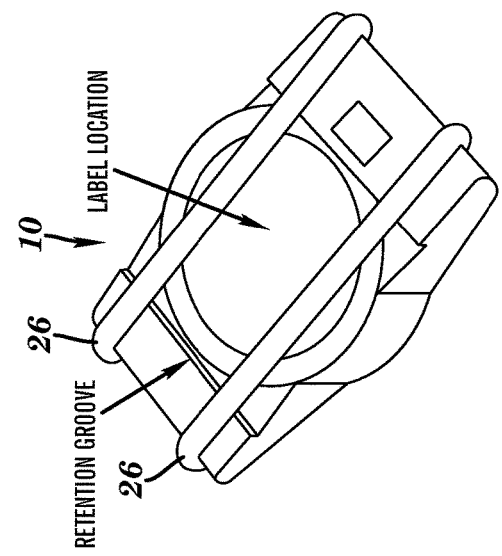
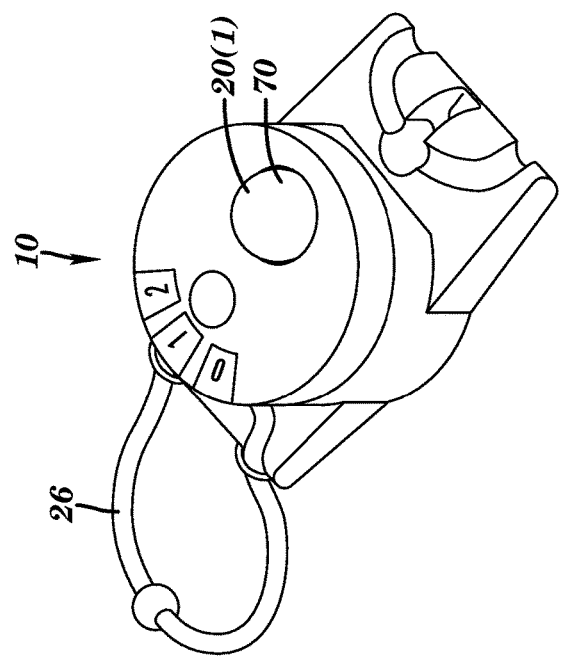
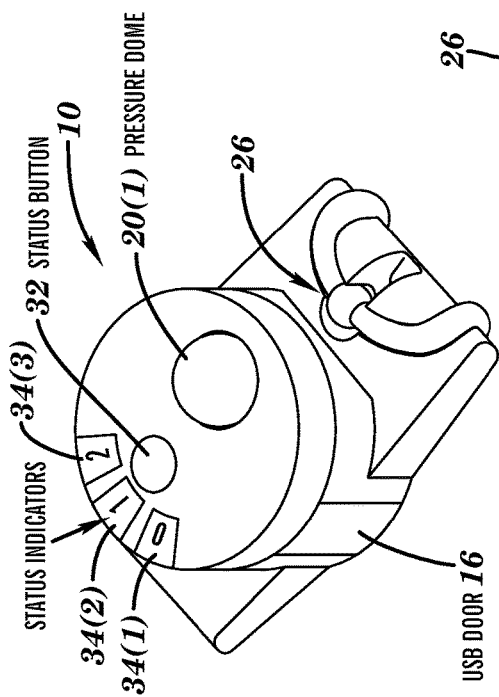
FIG. 2A
FIG. 2B
FIG. 2C

EVENT MONITORING DOSIMETRY APPARATUSES AND METHODS THEREOF

This application claims the benefit of U.S. Provisional Patent Application Ser. No. 61/446,369 filed Feb. 24, 2011, which is hereby incorporated by reference in its entirety.

This invention was made with government support under contract no. HR0011-10-C-0095 awarded by the DARPA. The government has certain rights in the invention.

FIELD

This technology generally relates to monitoring devices and methods and, more particularly, to event monitoring dosimetry apparatuses and methods thereof.

BACKGROUND

Traumatic brain injury (TBI) from an explosive blast remains a significant problem for military personnel, especially those involved in counter insurgency operations. Mild to moderate TBI may be difficult to detect immediately post event, with cognitive or motor deficits manifesting weeks or months post event.

Additionally, exposure to other types of blows and other types of events is a significant problem for other individuals as well. For example, recreational and professional athletes in many sport activities are routinely exposed to blows and other types of events with unknown individual or cumulative effects. Additionally, bike and motorcycle riders may experience some type of blow or other event by way of example only.

Currently, there is no widely deployed system to dose the exposure to an explosive blast, blow or other type of event. Given the nature of TBI, the wide variability in explosions, blows and other events and as well as the physical configurations during a blast events, and the variability in human response to each blast event, a widely deployed system to all personnel in a theater is needed to build a database of sufficient size to allow real-time dosimeter data to be used for triage and to monitor and assess military and non-military personnel depending on the particular application.

SUMMARY

A dosimetry apparatus includes at least one sensor in a housing, a cover configured to permit compression waves to pass through, the cover is seated over at the at least one sensor, and a dosimetry processing device with a memory. The dosimetry processing device is coupled to the at least sensor in the housing. The dosimetry processing device is configured to execute programmed instructions stored in the memory comprising: obtaining readings from the at least one sensor; storing the readings when obtained; conducting an analysis based on the obtained readings; and outputting at least one of the stored readings or the conducted analysis.

A dosimetry apparatus includes at least one of a pressure sensor or an inertial measurement unit in a housing, at least one of a mounting apparatus connected to the housing to mount the housing to an entity or a shock mounting apparatus that shock mounts the inertial measurement unit in the housing and a dosimetry processing device with a memory. The dosimetry processing device is coupled to the at least one of the pressure sensor or the inertial measurement unit in the housing. The dosimetry processing device is configured to execute programmed instructions stored in the memory comprising: obtaining readings from the at least one of the pressure sensor or the inertial measurement unit; storing the readings when obtained; conducting an analysis based on the obtained readings; and outputting at least one of the stored readings or the conducted analysis.

A method of making a dosimetry apparatus includes providing at least one sensor in a housing. A cover configured to permit compression waves to pass through is seated over at least the pressure sensor. A dosimetry processing device with a memory is coupled to the at least one sensor in the housing. The dosimetry processing device is configured to execute programmed instructions stored in the memory comprising: obtaining readings from the at least one sensor; storing the readings when obtained; conducting an analysis based on the obtained readings; and outputting at least one of the stored readings or the conducted analysis.

A method of making a dosimetry apparatus includes providing at least one of a pressure sensor or an inertial measurement unit in a housing. At least one of a mounting apparatus is connected to the housing to mount the housing to an entity or a shock mounting apparatus shock mounts the inertial measurement unit in the housing. A dosimetry processing device with a memory is coupled to the at least one of the pressure sensor or the inertial measurement unit in the housing. The dosimetry processing device is configured to execute programmed instructions stored in the memory including: obtaining readings from the at least one of the pressure sensor or the inertial measurement unit; storing the readings when obtained; conducting an analysis based on the obtained readings; and outputting at least one of the stored readings or the conducted analysis.

A dosimetry apparatus includes at least one sensor in a housing and at least one conductor is coupled to the at least one sensor and that extends out from the housing. A cover configured to permit compression waves to pass through is seated over at least the sensor and is connected to the housing.

A method for making a dosimetry apparatus includes providing at least one sensor in a housing and coupling at least one conductor that extends out from the housing to the at least one sensor. A cover configured to permit compression waves to pass through is seated over at least the sensor and is connected to the housing.

This technology provides a number of advantages including providing a more effective and efficient event monitoring dosimetry apparatus. With this technology, event data from a blast or blow can be captured and utilized to guide evaluation of exposed individuals. Additionally, this technology can capture and provide event data that will help to provide a better understanding the mechanisms of traumatic brain injury resulting from an explosive blast, blow, or other event. Further, the exemplary cover provides improved omni-directionality, while the exemplary shock mounting enables capture of peak accelerations with lower g-accelerometers. Even further, this technology provides effective omni-directionality pressure sensors without internal processing capabilities.

This technology can be used in a variety of different applications, such as for the military, sporting activities, and other daily activities by way of example only. For military applications, this technology could be helmet mounted, helmet strap mounted, worn on the torso, and/or mounted within vehicle cabins. For sporting activities, this technology could be mounted within helmets or on uniforms. For daily activities, this could be mounted to helmets used for bicycles and motorcycles by way of example.

BRIEF DESCRIPTION OF THE DRAWINGS

FIGS. 2A-2C are perspective view of the exemplary event monitoring dosimetry apparatus;

DETAILED DESCRIPTION

Figure 1:
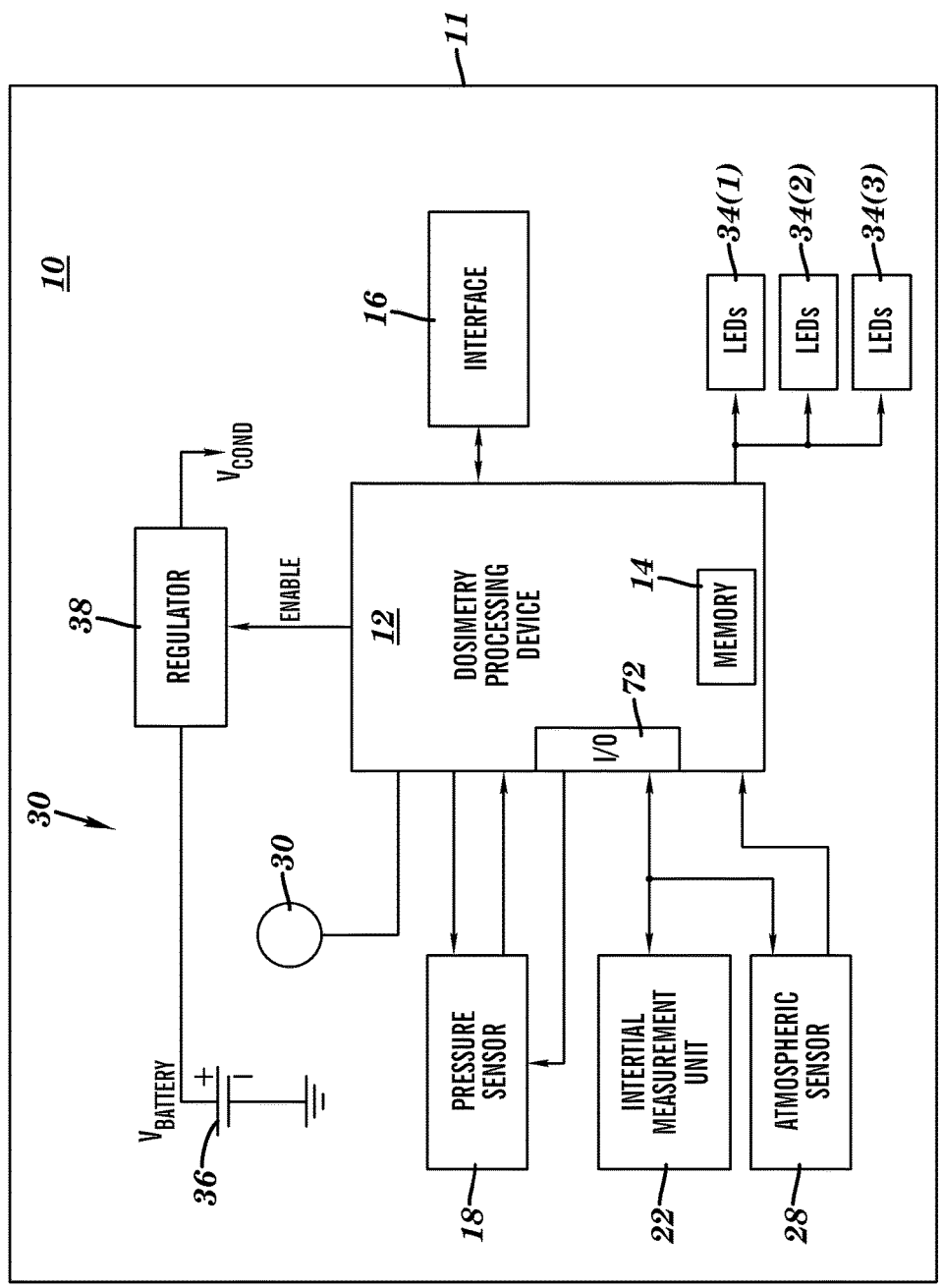
FIG. 1 is a diagram of an exemplary event monitoring dosimetry apparatus.
Figure 3:
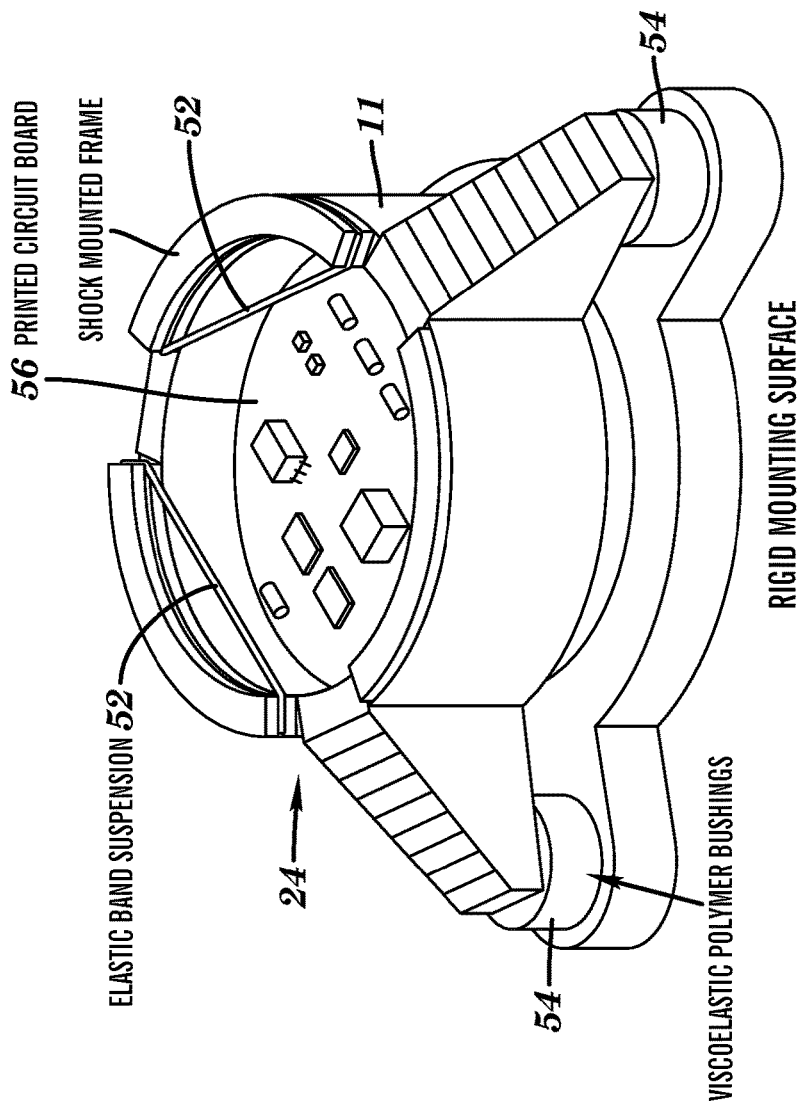
FIG. 3 is a perspective view of the shock mounting devices in the exemplary event monitoring dosimetry apparatus
Figure 4A:
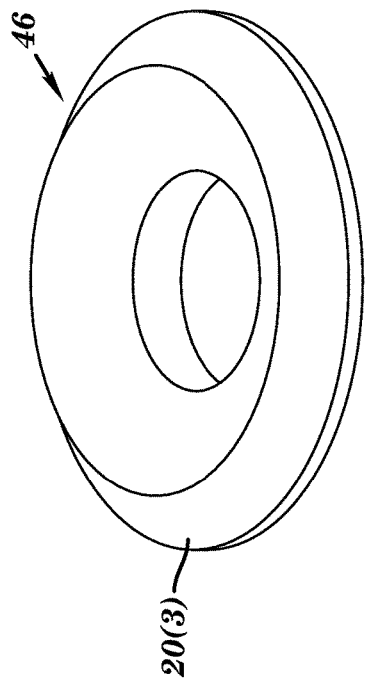
FIGS. 4A-4D are perspective views of different exemplary covers for an event monitoring dosimetry apparatus.
Figure 4B:
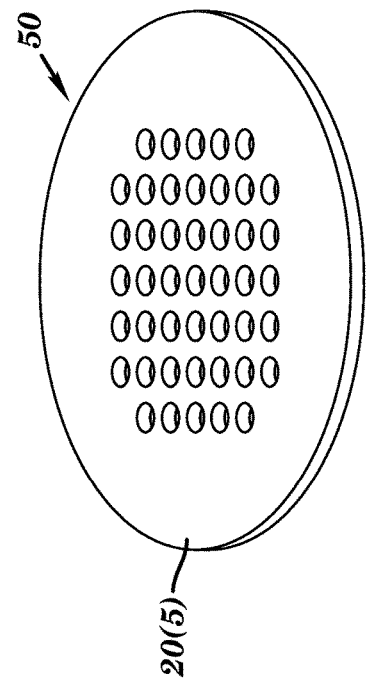
Figure 4C:
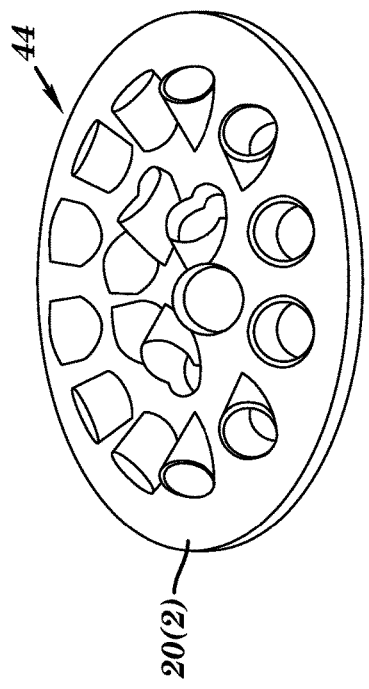
Figure 4D:
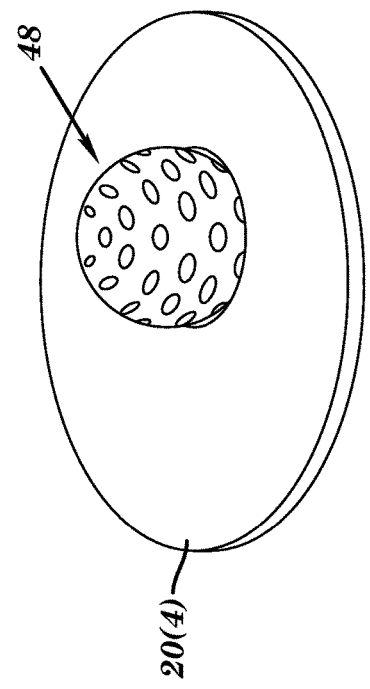

An exemplary event monitoring dosimetry apparatus 10 is illustrated in FIGS. 1-3. The event monitoring dosimetry apparatus 10 includes a housing assembly 11 with a dosimetry processing device 12 with a memory 14, an interface device 16, a pressure sensor 18, a cover 20(1), an inertial monitoring unit 22, shock mounting system 24, mounting system 26, an atmospheric sensor 28, a power system 30, an engagement device 32, and a series of different colored LEDs with different numeric indicators 34(1)-34(3), although the apparatus 10 could include other types and numbers of systems, devices, components and elements in other configurations. This technology provides a number of advantages including provide a more effective and efficient event monitoring dosimetry apparatus.

Figure 6:
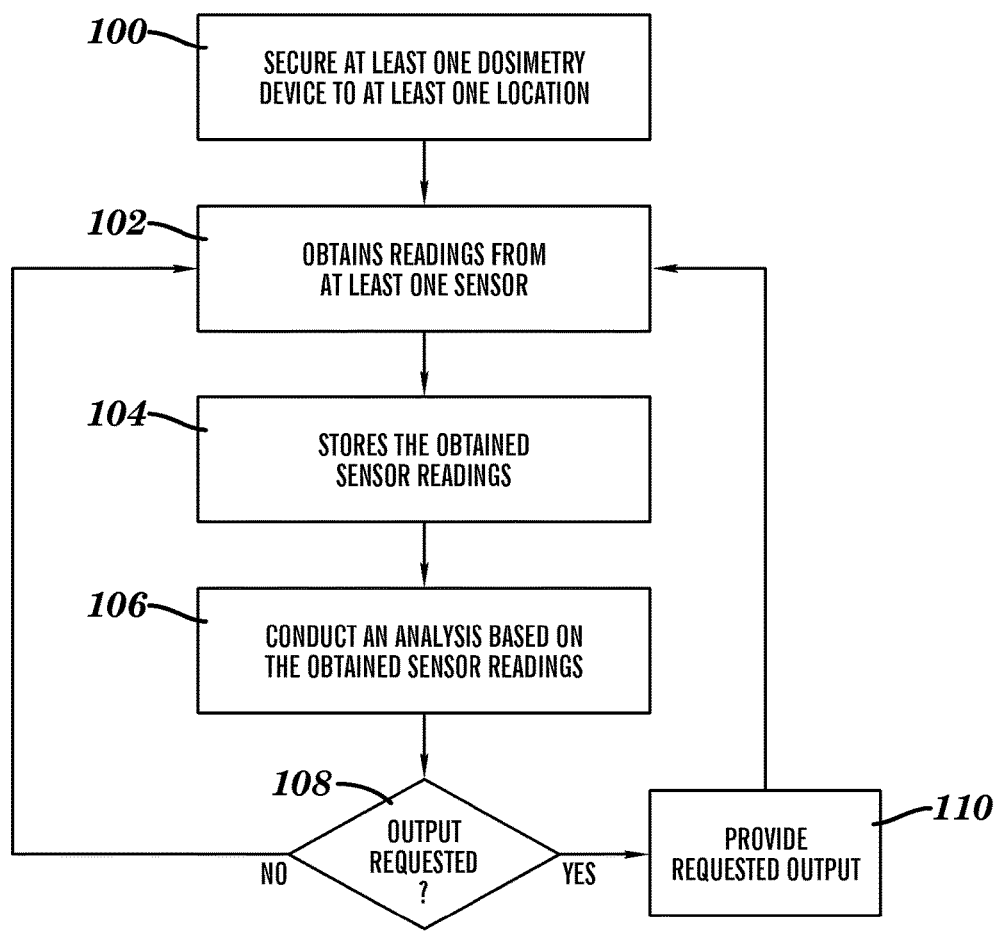
FIG. 6 is an exemplary method for monitoring events with the exemplary event monitoring dosimetry apparatus.

Referring more specifically to FIG. 1, the dosimetry processing device 12 comprises one or more processors internally coupled to the memory 14 by a bus or other links, although other numbers and types of systems, devices, components, and elements in other configurations and locations can be used. The one or more processors in the dosimetry processing device 12 executes a program of stored instructions for one or more aspects of the present technology as described and illustrated by way of the examples herein, although other types and numbers of processing devices and logic could be used and the processor could execute other numbers and types of programmed instructions. The memory 14 in the dosimetry processing device 12 stores these programmed instructions for one or more aspects of the present technology as described and illustrated herein, although some or all of the programmed instructions could be stored and executed elsewhere. A variety of different types of memory storage devices, such as a solid state memory, can be used for the memory 14 in the dosimetry processing device 12. The flow chart shown in FIG. 6 is representative of example steps or actions of this technology that may be embodied or expressed as one or more non-transitory computer or machine readable instructions stored in memory 14 that may be executed by the one or more processors.

The interface device 16 in the dosimetry processing device 12 is used to operatively couple and communicate between the dosimetry processing device 12 and one or more external computing or storage devices, although other types and numbers of communication networks or systems with other types and numbers of connections and configurations can be used.

Although an example of the dosimetry processing device 12 is described herein, it can be implemented on any suitable computer system or computing device. It is to be understood that the devices and systems of the examples described herein are for exemplary purposes, as many variations of the specific hardware and software used to implement the examples are possible, as will be appreciated by those skilled in the relevant art(s).

Furthermore, the system of the examples may be conveniently implemented using one or more general purpose computer systems, microprocessors, digital signal processors, and micro-controllers, programmed according to the teachings of the examples, as described and illustrated herein, and as will be appreciated by those ordinary skill in the art.

One or more aspects of examples may also be embodied as a non-transitory computer readable medium having instructions stored thereon for one or more aspects of the present technology as described and illustrated by way of the examples herein, as described herein, which when executed by a processor, cause the processor to carry out the steps necessary to implement the methods of the examples, as described and illustrated herein.

The pressure sensor 18 is coupled to the dosimetry processing device 12, although the pressures sensor 18 could be coupled to other types and numbers of devices. In this example, the pressure sensor 18 is a single pressure sensor to help achieve low cost and disposability parameters, although other types and numbers of pressure sensors could be used. Additionally, in this example the pressure sensor 18 is insensitive to direction and will substantially detect the same pressure waveform independent of the relative orientation of the pressure sensor 18 to the pressure front, although the pressure sensor could have other degrees of improved directional sensitivity, such as fifty percent or more by way of example only. To have multi-directional sensitivity, in this example the pressure sensor 18 is positioned below a wire mesh dome cover 20(1) which extends out and away from the housing 11, although other types of covers could be used to enable multi-directional sensing by the pressure sensor 18.

The mesh dome cover 20(1) comprises a very fine mesh layer, which acts as a filter for particles, sandwiched between two larger mesh layers used for structural strength, although the mesh dome cover 20(1) can be made with other types and numbers of layers. Additionally, the mesh dome cover 20(1) can be made of a variety of different types of materials, such as metallic materials, non-metallic materials, and fabric weaves as well as combinations of different materials by way of example only. Further, a floating body, such as a sphere or beads which are loose, other structures such as beads which are packed in and can not move or a porous matrix structure also may also be inserted within the mesh dome cover 20(1) to improve omni-directionality. Further, a check valve 70 can be situated within the mesh dome cover 20(1) to improve omni-directionality as shown in FIG. 2C.

By way of example only, other types of covers 20(2)-20(5) which could be seated over and utilized to assist with multi-directional sensitivity of the pressure sensor 18 are illustrated in FIGS. 4A-4D. For example: the cover 20(2) has a plurality of funnel shaped passages 44 angled towards the center; the cover 20(3) has a centralized funnel shaped structure 46 designed to direct the compression wave to the interior of the dosimetry apparatus 10; the cover 20(4) has a plastic dome 48 with perforations; and the cover 20(5) has a matrix of perforations 50 which all are designed to operate as cover 20(1) with or without any added structures as discussed above, although other types and numbers of covers with other shapes and configurations and which may incorporate a porous matrix to improve uniformity and/or fine mesh screen for dust exclusion could be used.

Referring back to FIG. 1, the inertial monitoring unit 22 is a low-g (for example 16 g) three-axis accelerometer to capture linear acceleration in three axes, although other types (such as a high-g accelerometer, for example >100 g) and numbers of inertial measurement units could be used. For example, the inertial measurement unit 22 could be a gyroscope which records rotational acceleration. To account for differences in pressure readings from the pressure sensor 18 which depend on the incident direction of the force, the three-axis acceleration information from the inertial monitoring unit 22 can be used by the dosimetry processing device 12 to determine the vector of movement coincident with the arrival of the pressure shock front. This indicates the relative angle of the dosimetry apparatus 10 to the force allowing for compensation of the measured pressure profile including the levels of the stored reading thresholds to improve accuracy and precision with respect to the obtained readings and the identification of events.

Referring to FIG. 3, the shock mounting system 24 is used to suspend a printed circuit board 56 which has the dosimetry processing device 12 with the memory 14, the interface device 16, the pressure sensor 18, the inertial monitoring unit 22, the atmospheric sensor 28, and the power system 30 in the housing 11, although other types and numbers of elements and other components could be on the printed circuit board and suspended. The result is an expansion of the dynamic range of the dosimetry apparatus 10 at the expense of resolution. The physical gap between the printed circuit board 56 and the housing 11 is determined by the mass and maximum acceleration impulse.

In this example, the shock mounting system 24 includes elastic suspension devices 52 and viscoelastic polymer bushings 54, although the apparatus 24 can include other types and numbers of shock mounting systems, such as a grease damping system. Additionally, in this example the printed circuit board 56 is suspend by three points using the elastic suspension devices 52, although the printed circuit board 56 could be suspended by other numbers of points in other manners and other systems, device, and components could be suspended, such as just the inertial monitoring unit 22. The use of the two attenuation schemes with the shock mounting system 24, such as the elastic suspension devices 52 and the viscoelastic polymer bushings 54 in this example, provides a multiplicative effect reducing the requirements on each of these shock mounting systems. This also reduces the required space between the printed circuit board 56 and the housing 11 which reduces the overall size of the dosimetry apparatus 10.

Referring to FIG. 2C, the mounting system 26 is used to mount the housing 11 of the dosimetry apparatus 10 to an entity, such as an object or person. In this example, the mounting system 26 comprises a strap that can be mounted to a helmet strap or fabric webs on uniforms, although other types of mounting systems 26 could be used. The helmet strap for the mounting system 26 must be non-stiff/flexible/elastomeric, so as to damp any incident vibration/shock, but short enough and well fixed enough to couple the dosimeter effectively into the mass you are trying to measure. Detachably/compliantly mounting of the dosimeter apparatus 10 with a mounting system 26, such as the illustrated helmet strap by way of example allows mounting more directly to a lower stiffness location which in turn couples the dosimetry apparatus 10 into a higher mass than traditional helmet mounting. This coupling provides more significant acceleration measurements for risk injury assessment than connection to a detached part of a wearer, such as a helmet. Both the lower stiffness of the mounting strap and the higher mass the dosimetry apparatus 10 is attached to are part of the lower resultant acceleration.

By way of example only, other types of mounting systems 26 may include adhesive, hook and loop mating fasteners, fabric wraps with hook and loop mating fasteners, elastic straps with or without snaps, hooks, grommet snaps embedded in the housing and attached to a helmet strap, and non-elastic straps with a tightening mechanism. The manners by which these attachment mechanisms operate are well known to those ordinary skill in the art and thus will not be described in detail here. For example, the elastic strap can comprise an elastic loop that hooks onto a portion of the housing 11, wraps around the desired entity, and attaches to another portion of the housing to secured the housing 11.

The atmospheric sensor 28 is coupled to the dosimetry processing device 12 and provides atmospheric readings within the dosimetry apparatus 10, although other types and numbers of atmospheric monitors could be used and the atmospheric sensor 28 could be positioned to take other readings The power system 30 includes a battery 36 coupled to a regulator 38 which is coupled to the dosimetry processing device 12, although other types of power systems with other types and numbers of components, such as one with an energy harvester and/or without a regulator 38 could be used. The regulator 38 is coupled to regulate power provided by the battery 36 to the dosimetry processing device 12. Additionally, in this example power for the pressure sensor 18, the inertial measurement unit 22, the atmospheric sensor 28, and/or the strain gauge 29 is coupled directly from the dosimetry processing device 12 to save power, although other types and numbers of devices and systems could be coupled directly to the dosimetry processing device 12 to provide power. Additional, power management may be achieved through stored programmed instructions executed by the dosimetry processing device 12 for a standard monitoring mode, a lower power monitoring mode and a sleep mode, although other types and numbers of modes can be used. The inertial measurement unit 22 provides data to the dosimetry processing device 12 to identify periods of inactivity to trigger the lower power standby mode when minimal activity is identified or sleep mode when prolong periods of inactivity are identified for power savings. Activity sensing by the inertial measurement unit 22 enables the dosimetry processing device 12 to switch to standard monitoring mode with a high sampling rate for the inertial measurement unit 22 and pressure sensor 18 by way of example. In this example, all peripheral devices, such as pressure sensor 18, inertial measurement unit 22, and atmospheric sensor 28 by way of example only, are powered through digital input/output (I/O) pins 72 on the processor in the dosimetry processing device 12 rather than from a power bus. This allows peripheral devices to be turned off via the processor in the dosimetry processing device 12 saving power. The regulator 38 is enabled through an I/O input/output (I/O) pin on the processor in the dosimetry processing device 12. This allows the dosimetry processing device 12 to be completely turned off to extend shelf life. The dosimetry processing device 12 is activated either through the button or powering through USB The engagement device 32, such as a button by way of example only, is coupled to the dosimetry processing device 12, although the engagement device could be coupled in other manners. The engagement device 32 can be used to request an output of readings including of identified events, stored events and/or assessments of the readings. Additionally, other types and numbers of mechanisms for engaging the dosimetry processing device 12 can be used, such as another computing device coupling to the dosimetry processing device 12 through the interface 16 to request and obtain output data and other information, download a time and date stamp, set and/or reprogram criteria and other parameters by way of example only.

The series of different colored LEDs with different numeric indicators 34(1)-34(3) are used to provide a status indication for the output stored readings and of the assessment of the stored readings associated with identified events to provide immediate triage of the severity of an event, although other types and numbers of displays which provide other types of outputs can be used. In this example, LED 34(1) is green colored and has a numeric indicator of zero, LED 34(2) is yellow colored and has a numeric indicator of one, and LED 34(1) is red colored and has a numeric indicator of two, although other colors and symbols could be used.

Figure 5B:
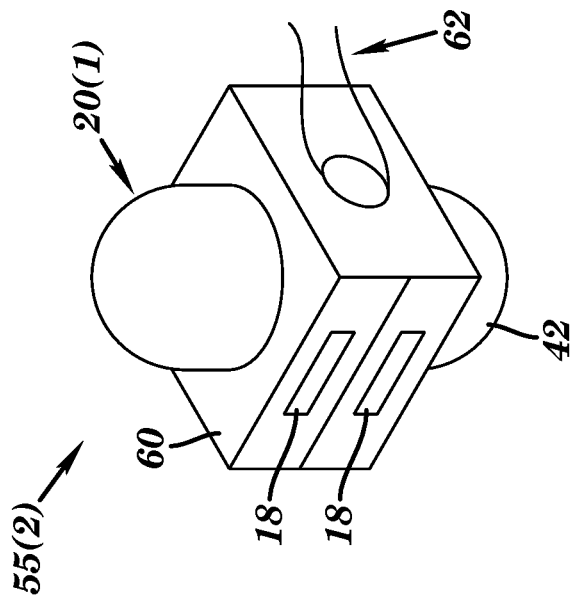
FIGS. 5A-5B are perspective views of exemplary dosimetry pressure sensors.
Figure 5A:
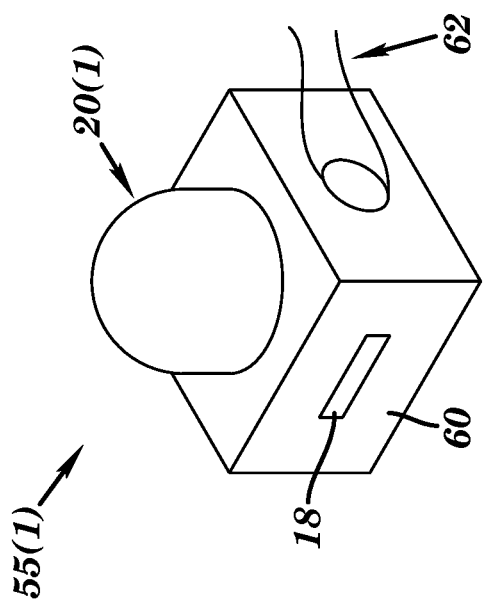

Referring to FIGS. 5A-5B examples of dosimetry pressure sensing apparatuses 55(1) and 55(2) are illustrated. The dosimetry pressure sensing apparatuses 55(1) and 55(2) are the same as the dosimetry apparatus 10, except as described and illustrated herein. In this example, the dosimetry pressure sensing apparatus 55(1) has a pressure sensor 18 in a housing 60 with a cover 20(1) seated over the pressure sensor 18, although the dosimetry pressure sensing apparatuses could have other numbers and types of system, devices and elements in other configurations. Additionally, the dosimetry pressure sensing apparatuses 55(1) has conductors 62 coupled to the pressure sensor 18 extending out from the housing 60 to couple to an external processing device as opposed to the internal processing device 12 in dosimetry apparatus 10. Additionally, in this example, the dosimetry pressure sensing apparatus 55(2) has two pressure sensors 18 on opposing sides of the housing 60 with a cover 20(1) seated over each of the pressure sensors 18, although the dosimetry pressure sensing apparatuses could have other numbers and types of system, devices and elements in other configurations, such as other locations for and numbers of pressure sensors. Additionally, the dosimetry pressure sensing apparatuses 55(2) has conductors 62 coupled to each of the pressure sensors 18 extending out from the housing 60 to couple to an external processing device as opposed to the internal processing device 12 in dosimetry apparatus 10.

Referring to FIG. 6, an exemplary method for monitoring events with the exemplary event monitoring dosimetry apparatus will now be described. At step 100, at least one dosimetry apparatus 10 is secured using the mounting system 26 to a location on an object, although other types and manners for securing the one or more dosimetry apparatuses 10 to the object can be used.

In step 102, the dosimetry processing device in the dosimetry apparatus 10 obtains readings from a single pressure sensor 18 and the inertial measurement unit 22, although the dosimetry apparatus 10 can obtain readings from other types and numbers of sensors. In this example, the pressure sensor 18 is a single pressure sensor which obtains pressure readings, although other types and numbers of pressure sensors could be used. Additionally, in this example, the inertial measurement unit 22 is a three-axis accelerometer which obtains linear acceleration readings in real time, although other types of inertial measurement units can be used, such as a gyroscope which obtains rotational acceleration readings.

In step 104, the dosimetry processing device 12 stores the obtained pressure readings from the pressure sensor 18, acceleration readings from the inertial measurement unit 22, and atmospheric readings from the atmospheric sensor 28, although other types and amounts of readings and other data could be stored in other locations and manners.

In step 106, the dosimetry processing device 12 also may conduct an analysis based on the obtained pressure readings, acceleration readings and/or atmospheric readings, although other types and numbers of analyses based on other readings and data can be performed. Additionally, the dosimetry processing device 12 assesses the severity of the event based on the obtained pressure readings, acceleration readings, and/or atmospheric readings, although other manners for conducting an analysis can be used. The dosimetry processing device 12 stores the conducted analysis and assessed severity in memory 14, although the conducted analyses assessed severity can be stored in other locations and manners.

In step 108, the dosimetry processing device 12 determines whether an output is requested, such as by activation of the engagement device 32 or a request via the interface 16, such as a USB, from another computing device, although other manners for output requests could be used. The activating of the engagement device could trigger a display on one of the LEDs 34(1)-34(3), although other types of outputs could be triggered, such as an output of data and other information. The engagement device 32 also can have other functions, such as providing outputting different information based on a number of times the button is pressed or the length of time the button is pressed or powering on or off the dosimetry apparatus 10. The request for data through the interface 16 from another computing device can be for all or requested portions of the stored data. If in step 108, the dosimetry processing device 12 determines an output has not been requested, then the No branch is taken back to step 102 as described earlier. If in step 108, the dosimetry processing device 12 determines an output has been requested, then the Yes branch is taken back to step 110. In step 110, the dosimetry processing device 12 provides the requested output, such as a display on one of the LEDs 34(1)-34(3) or an output of one or more of the stored readings, the identified event, a determined injury risk assessment based on the conducted analysis, data relating to switches between power modes, data relating to output requests, and/or identified false positive events and related data by way of example only via the interface 16, although the information could be output to other devices, other types and amounts of information and other data could be provided and the information and data can be obtained in other manners, such as through a connection with another computing device interacting with the dosimetry processing device 12 via the interface 16. In this example, the dosimetry processing device 12 can output the identified event with determined injury risk assessment based on the conducted analysis by illumination of one of the LEDs 34(1) with a numeric indicator in response to the activation by the engagement device 32, although other types and amounts of information could be provided. For example, if the determined injury risk assessment for the identified event is moderate, e.g. within a first range of one or more of the first thresholds then the yellow colored LED 34(2) with the numeric indicator of one is illuminated/flashed. If the determined injury risk assessment for the identified event is severe, e.g. above a first range of one or more of the first thresholds then the red colored LED 34(3) with the numeric indicator of two is illuminated/flashed. If there is no event recorded, the green colored LED 34(1) with the numeric indicator of zero is illuminated. Additionally, a requested output could trigger the dosimetry processing device 12 to output the stored readings, determined direction and other data described in the examples herein with or without the assessment information via the interface device 16 to another computing device. Next, this method can return back to step 102 until the exemplary dosimetry apparatus 10 is turned off or the power runs out.

Accordingly, as illustrated and described with reference to the examples herein this technology provides a more effective and efficient event monitoring dosimetry apparatus. With this technology, event data from a blast or blow can be captured and utilized to provide real time analysis of exposed individuals. Additionally, this technology can capture and provide event data that will help to provide a better understanding the mechanisms of traumatic brain injury resulting from an explosive blast, blow, or other event

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A multiple use dosimetry apparatus comprising:
   a pressure sensor capable of detecting a blast pressure waveform disposed in a housing;
   a cover configured to permit blast compression waves to pass through, the cover which extends out and away from the housing is seated over the pressure sensor and comprises a mesh structure comprising a particle filtering mesh layer configured to exclude dust seated against a structural mesh layer configured to provide structural integrity to the particle filtering mesh layer, wherein the structural mesh layer comprises larger mesh openings than the mesh openings of the particle filtering mesh layer in a manner that protects the pressure sensor and the particle filtering mesh layer from physical damage; and
   a dosimetry processing device with a memory coupled to the pressure sensor in the housing, the dosimetry processing device configured to execute programmed instructions stored in the memory comprising obtaining readings from the pressure sensor, storing the readings when obtained, conducting an analysis based on the obtained readings and outputting at least one of the stored readings or the conducted analysis, wherein the pressure sensor combined with the cover provides multi-directional sensitivity to blast direction and will detect the same pressure waveform independent of the relative orientation of the pressure sensor to the pressure front of the explosive blast to within fifty percent of the pressure waveform amplitude.

2. The apparatus as set forth in claim 1 wherein the cover has one or more shaped passages that direct the compression waves towards the pressure sensor.

3. The apparatus as set forth in claim 2 wherein the one or more shaped passages of the cover comprise a funnel shape.

4. The apparatus as set forth in claim 1 wherein the mesh structure further comprises a check valve that controls flow into the housing.

5. The apparatus as set forth in claim 1 further comprising a floating body seated within the mesh structure.

6. The apparatus as set forth in claim 1 further comprising beads packed between the mesh structure and the pressure sensor.

7. The apparatus as set forth in claim 1 further comprising a porous matrix between the pressure sensor and the mesh structure.

8. The apparatus as set forth in claim 1 further comprising an inertial measurement unit in the housing.

9. The apparatus as set forth in claim 1 further comprising a display device coupled to the dosimetry processing device, the display device configured to illustrate the stored readings.

10. The apparatus as set forth in claim 9 wherein the display device comprises a plurality of different colored status indicator devices each with a different symbol to illustrate a severity level of the stored reading.

11. The apparatus as set forth in claim 10 further comprising an engagement device coupled to the dosimetry processing device, wherein the dosimetry processing device is configured to execute programmed instructions stored in the memory further comprising providing a status indicator of the stored readings on the display device in response to an activation of the engagement device.

12. The apparatus as set forth in claim 1 further comprising coupling power for the at least one peripheral device directly from the dosimetry processing device.

13. The apparatus set forth in claim 1, further comprising a conductor coupled to the sensor and extending out from the housing, wherein the conductor is fashioned to couple to a processing device external to the dosimetry apparatus.

14. A method of making a multiple use dosimetry apparatus, the method comprising:
    providing a pressure sensor capable of detecting a blast pressure waveform disposed in a housing;
    seating a cover configured to permit blast compression waves to pass through, the cover which extends out and away from the housing is seated over the pressure sensor and comprises a mesh structure comprising a particle filtering mesh layer configured to exclude dust seated against a structural mesh layer configured to provide structural integrity to the particle filtering mesh layer, wherein the structural mesh layer comprises larger mesh openings than the mesh openings of the particle filtering mesh layer in a manner that protects the pressure sensor and the particle filtering mesh layer from physical damage; and
    coupling a dosimetry processing device with a memory to the pressure sensor in the housing, the dosimetry processing device configured to execute programmed instructions stored in the memory comprising obtaining readings from the pressure sensor, storing the readings when obtained, conducting an analysis based on the obtained readings, and outputting at least one of the stored readings or the conducted analysis, wherein the pressure sensor combined with the cover provides multi-directional sensitivity to blast direction and will detect the same pressure waveform independent of the relative orientation of the pressure sensor to the pressure front of the explosive blast to within fifty percent of the pressure waveform amplitude.

15. The method as set forth in claim 14 wherein the cover has one or more shaped passages that direct the compression waves towards the at least one sensor.

16. The method as set forth in claim 15 wherein the one or more shaped passages of the cover comprise a funnel shape.

17. The method as set forth in claim 14 further comprising providing a check valve under the mesh structure that controls flow into the housing.

18. The method as set forth in claim 14 further comprising providing a floating body within the mesh structure.

19. The method as set forth in claim 14 further comprising beads packed between the pressure sensor the mesh structure.

20. The method as set forth in claim 14 further comprising a porous matrix between the pressure sensor and the mesh structure.

21. The method as set forth in claim 14 further comprising an inertial measurement unit in the housing.

22. The method as set forth in claim 14 further comprising coupling a display device to the dosimetry processing device, the display device configured to illustrate the stored readings.

23. The method as set forth in claim 22 wherein the display device comprises a plurality of different colored status indicator devices each with a different symbol to illustrate a severity level of the stored readings.

24. The method as set forth in claim 23 further comprising coupling an engagement device to the dosimetry processing device, wherein the dosimetry processing device is configured to execute programmed instructions stored in the memory further comprising providing a status indicator of the stored readings on the display device in response to an activation of the engagement device.

25. The method as set forth in claim 14 further comprising coupling the at least one sensor to receive power directly from the dosimetry processing device.

* * * * *